(12) United States Patent
Koorevaar et al.

(10) Patent No.: US 9,072,271 B2
(45) Date of Patent: *Jul. 7, 2015

(54) **AGRONOMICALLY ELITE LETTUCE WITH QUANTITATIVE *BREMIA LACTUCA* RESISTANCE**

(75) Inventors: Gerard N. Koorevaar, Ede (NL); Hieronymus J. M. van der Laan, Wageningen (NL); Rosa I. Weber, Wageningen (NL)

(73) Assignee: Seminis Vegetable Seeds, Inc., Woodland, CA (US)

( * ) Notice: Subject to any disclaimer, the term of this patent is extended or adjusted under 35 U.S.C. 154(b) by 550 days.

This patent is subject to a terminal disclaimer.

(21) Appl. No.: 13/352,162

(22) Filed: Jan. 17, 2012

(65) Prior Publication Data
US 2012/0204290 A1 Aug. 9, 2012

Related U.S. Application Data

(62) Division of application No. 12/398,737, filed on Mar. 5, 2009, now Pat. No. 8,124,833.

(60) Provisional application No. 61/033,823, filed on Mar. 5, 2008.

(51) Int. Cl.
*A01H 5/00* (2006.01)
*A01H 5/12* (2006.01)

(52) U.S. Cl.
CPC ........................................ *A01H 5/12* (2013.01)

(58) Field of Classification Search
None
See application file for complete search history.

(56) References Cited

U.S. PATENT DOCUMENTS 8,124,833 B2 * 2/2012 Koorevaar et al. ............ 800/260

OTHER PUBLICATIONS

Jeuken et al, Theor Appl Genet (2008) 116:845-857.*
Bonnier et al., "New sources of major gene resistance in lactuca to *Bremia lactucae*," *Euphytica*, 61:203-211, 1992.

Grube et al., "Comparative genetic analysis of field resistance to downy mildew in the lettuce cultivars 'Grand Rapids' and 'Iceberg'," *Euphytica*, 142:205-215, 2005.
Gustafsson, "Potential sources of resistance to lettuce downy mildew (*Bremia lactucae*) in different *Lactuca* species," *Euphytica*, 40:227-232, 1989.
Jeuken et al., "An integrated interspecific AFLP map of lettuce (*Lactuca*) based on two *L. sativa* x *L. saligna* F2 populations," *Theor Appl Genet*, 103:638-647, 2001.
Jeuken et al., "Efficient QTL detection for nonhost resistance in wild lettuce: backcross inbred lines versus F2 population," *Theor Appl Genet*, 116:845-857, 2008.
Jeuken et al., "*Lactuca saligna*, a non-host for lettuce downy mildew (*Bremia lactucae*), harbors a new race-specific Dm gene and three QTLs for resistance," *Theor Appl. Genet*, 105:384-391, 2002.
Jeuken et al., "The development of lettuce backcross inbred lines (BILs) for exploitation of the *Lactuca saligna* (wild lettuce) germplasm," *Theor Appl. Genet*, 109:394-401, 2004.
Lebeda et al., "Aspects of the interactions between wild lettuce spp. and related genera and lettuce down mildew (*Bremia lactucae*)," In: Advances in Downy Mildew Research, pp. 85-117, Jeger et al. (Eds.), Kluwer Academic Publishers, Dordrecht, 2002.
Lebeda et al., "Diversity of defence mechanisms in plant-oomycete interactions: a case study of *Lactuca* spp. and *Bremia lactucae*," *Eur. J. Plant Pathol*, 122:71-89, 2008.
Lebeda et al., "Histological characterization of resistance in *Lactuca saligna* to lettuce downy mildew (*Bremia lactucae*)," *Physiological and Molecular Plant Pathology*, 44:125-139, 1994.
Netzer et al., "*Lactuca saligna* L., a new source of resistance to downy mildew (*Bremia lactucae* reg.)," *HortScience*, 11(6):612-613, 1976.
Jueken et al., The genetics of non-host resistance to the lettuce pathogen *Bremia lactucae* in *Lactuca saligna*, Ph.D Thesis, Wageningen Univ. Dissertation #3203, ISBN 90-5808-619-4, 2002.
Zhang et al., "Genetic dissection of non-host resistance in lettuce to downy mildew: numerous resistance QTLs detected during plant development," *Plant Pathology*, 58(5):923-932, 2009.
Zhang et al., "Three Combined Quantitative trait loci from nonhost *Lactuca saligna* are sufficient to provide complete resistance of lettuce against *Bremia lactucae*," *MPMI*, 22(9):1160-1168, 2009.

\* cited by examiner

*Primary Examiner* — Eileen B O Hara
(74) *Attorney, Agent, or Firm* — Dentons US LLP; Alissa Eagle, Esq.

(57) ABSTRACT

The invention provides compositions and methods relating to the separation of quantitative Downy Mildew resistance traits from linked but undesirable agronomic traits. The invention further provides plants, plant parts, and seeds comprising such Downy Mildew Resistance traits, which do not comprise alleles specifying undesirable agronomic traits that are genetically linked to the resistance traits.

13 Claims, 11 Drawing Sheets

FIG. 5
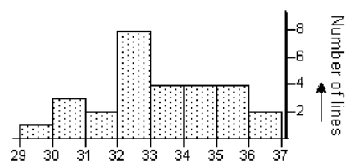
Histogram of average plant diameter for 28 F3 lines. Diameter (in cm) was measured 40 days after planting.
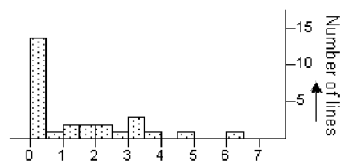
Histogram of average number of adventitious shoots for 28 F3 lines. Number of adventitious shoots was measured 40 days after planting.
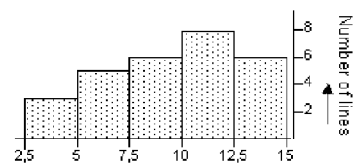
Histogram of average bolting date for 28 F3 lines. Value is days after June 20 which 47 days after planting.

FIG. 6

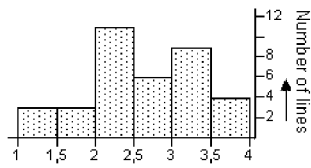

Histogram of average *Bremia lactuca* resistance score for 36 F3 lines. Score has been assessed on a 1 to 5 scale. 1 = resistant and 5 is susceptible and was measured 41 days after planting.

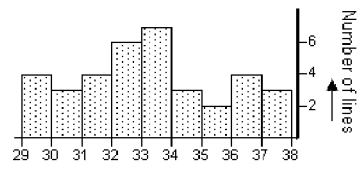

Histogram of average plantdiameter (in cm) for 36 F3 lines. Measurement was done 44 days after planting.

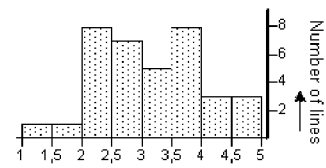

Histogram of average leaf bubbel score for 36 F3 lines. Score has been assessed on a 1 to 5 scale. 1 = almost fat leaves, like Sylvesta and 5 = most bubbled fenotypes like BIL6.3. Measurement has been done 47 days after planting.

Sylvesta   olof   BIL6.3   Line Q6-712 with *L. saligna* introgression from LE3118 to LE9214

US 9,072,271 B2

AGRONOMICALLY ELITE LETTUCE WITH QUANTITATIVE BREMIA LACTUCA RESISTANCE

This application is a division of U.S. application Ser. No. 12/398,737, filed Mar. 5, 2009, now U.S. Pat. No. 8,124,833 which application claims the benefit of priority of U.S. Provisional Appl. Ser. No. 61/033,823, filed Mar. 5, 2008, each of the entire disclosures of which are incorporated herein by reference in their entireties.

INCORPORATION OF SEQUENCE LISTING

The sequence listing that is contained in the file named "SEMS041US_seq_ST25.txt", which is 2.56 kilobytes (as measured in Microsoft Windows®) and was created on Mar. 4, 2009, is filed herewith by electronic submission and is incorporated by reference herein.

BACKGROUND OF THE INVENTION

1. Field of the Invention

The present invention relates to the field of plant breeding and, more specifically, to the development of downy mildew-resistant lettuce having elite agronomic traits.

2. Description of Related Art

Cultivated lettuce, *Lactuca sativa*, is a temperate annual or biennial plant most often grown as a leaf vegetable. Lettuce belongs to the family Asteraceae (or Compositae). Other members of this family include endive, chicory, artichoke, sunflower and safflower. It is closely related to common wild lettuce or prickly lettuce (*L. serriola*) and less closely related to two other wild lettuces (*L. saligna* and *L. virosa*). Cultivated lettuce and sunflower are the best genetically characterized members of this family. Four principal types of cultivated lettuce include crisphead (mostly iceberg), romaine (cos), leaf and butterhead. Each of these basic groups is comprised of numerous cultivars, each characterized by its own particular morphology, cultural adaptations, and disease resistance. Lettuce cultivars are susceptible to a number of diseases such as Downy Mildew, Sclerotinia Rot, Botrytis Rot, Corky Root Rot, Bacterial leafspot of lettuce, caused by *Xanthomonas campestris* pv. *vitians*, and lettuce mosaic virus, among others. Among the most important fungal diseases of lettuce is Downy Mildew, caused by *Bremia lactucae* (Regel). *L. saligna* displays quantitative resistance to *Bremia lactucae* such that it is generally considered to be a non-host plant of this oomycete, and has been studied as a potential source of genetic resistance to this disease.

SUMMARY OF THE INVENTION

The inventors have unexpectedly developed methods, using a combination of molecular and phenotyping tests, that produce lines that have quantitative resistance to *Bremia lactucae* but do not have the additional deleterious phenotypes previously associated with the resistance phenotype. In one aspect, the invention provides a lettuce plant comprising (a) a RBQ5 allele of *Lactuca saligna* conferring quantitative resistance to *Bremia lactucae*, wherein the plant lacks an allele genetically linked to the RBQ5 allele in *Lactuca saligna* conferring adventitious shoots, or (b) a RBQ6 allele of *Lactuca saligna* conferring quantitative resistance to *Bremia lactucae*, wherein the plant lacks an allele genetically linked to the RBQ6 allele in *Lactuca saligna* conferring reduced plant diameter or bubbled leaves. In a particular embodiment, the invention provides a lettuce plant defined as comprising the RBQ5 allele and the RBQ6 allele.

In other embodiments, the lettuce plant is defined as comprising an introgressed *L. saligna* region comprising an LE1244 allele. The plant may also lack an *L. saligna* LE1219 and/or LE0115 allele. In another embodiment, the plant may be defined as comprising an introgressed *L. saligna* region comprising an LE9214 and/or LE0017 allele. The plant may further lacks an *L. saligna* LE0420 allele. In specific embodiments, a plant of the invention may be defined as comprising any one or more allele selected from an LK1475, LE1276, LE3118, LE9214, LE0420 and/or LE0350 allele. In further embodiments, the lettuce plant may further be defined as comprising at least one additional gene that confers resistance to *Bremia lactucae*, wherein the gene is selected from the group consisting of DM1-DM16 and R17-R40.

In still further embodiments, the invention provides a seed or other plant part of the lettuce plant, selected from the group consisting of: a cell, a seed, a root, a stem, a leaf, a head, a flower, and pollen; wherein the seed or other plant part comprises one or both of the RBQ5 allele and RBQ6 allele.

In certain embodiments, a lettuce plant is provided that expresses all of the physiological and morphological characteristics of lettuce designation 50066390, a sample of seed of said designation having been deposited under ATCC Accession Number PTA-9045, or the plant expresses all of the physiological and morphological characteristics of lettuce designation 50070045, a sample of seed of said designation having been deposited under ATCC Accession Number PTA-9046. In specific embodiments, a lettuce plant is provided that is a progeny plant of any generation of lettuce designation 50066390 or lettuce designation 50070045, wherein the lettuce plant inherits from the designation 50066390 or 50070045 a RBQ6 allele of *Lactuca saligna* conferring quantitative resistance to *Bremia lactucae* and lacking an allele genetically linked to the RBQ6 allele in *Lactuca saligna* that confers reduced plant diameter or bubbled leaves, or a RBQ5 allele of *Lactuca saligna* conferring quantitative resistance to *Bremia lactucae* and lacking an allele that is genetically linked to the RBQ5 allele in *Lactuca saligna* and confers adventitious shoots, respectively.

In another aspect, the invention provides a method for obtaining a *Lactuca* plant comprising quantitative resistance to *Bremia lactucae*, comprising: (a) obtaining a *Lactuca* plant heterozygous for: (1) a RBQ5 allele from *Lactuca saligna* that confers quantitative resistance to *Bremia lactucae* and is genetically linked in the plant to a *Lactuca saligna* allele that confers adventitious shoots, or (2) a RBQ6 allele of *Lactuca saligna* that confers quantitative resistance to *Bremia lactucae* and is genetically linked in the plant to a *Lactuca saligna* allele that confers reduced plant diameter or bubbled leaves, wherein the plant is heterozygous relative to a corresponding locus in *Lactuca sativa*; (b) obtaining progeny of the plant; and (c) selecting at least a first progeny plant in which recombination has occurred such that the progeny comprises: (1) the RBQ5 allele but not the allele that confers adventitious shoots, or (2) the RBQ6 allele but not the allele that confers reduced plant diameter or bubbled leaves.

In one embodiment, the method relating to selecting the progeny plant comprises identifying a progeny plant that (1) comprises a genetic marker genetically linked to the RBQ5 allele in *L. saligna* and/or lacks a genetic marker present at the corresponding locus from *L. sativa*, and (2) lacks a genetic marker genetically linked to the allele that confers adventitious shoots in *L. saligna* and/or comprises a genetic marker present at the corresponding locus from *L. sativa*.

In another embodiment, the method relating to selecting the progeny plant comprises identifying a progeny plant that (1) comprises a genetic marker genetically linked to the RBQ6 allele in *L. saligna* and/or lacks a genetic marker present at the corresponding locus from *L. sativa*, and (2) lacks a genetic marker genetically linked to the allele that confers reduced plant diameter or bubbled leaves in *L. saligna* and/or comprises a genetic marker present at the corresponding locus from *L. sativa*.

In particular embodiments, the method may comprise selecting a progeny plant by detecting at least one allele selected from the group consisting of: an LK1475 allele, an LE0142 allele, an LE1244 allele, an LE7003 allele, an LE1276 allele, an LE0350 allele, an LE1219 allele, an LE0115 allele, an LE0204 allele, an LE1211 allele, an LE0428 allele, an LE0420 allele, an LE9214 allele, an LE0017 allele, an LK1413 allele, and an LE3118 allele, wherein the progeny plant (1) comprises a genetic marker genetically linked to the RBQ5 allele in *L. saligna* and/or lacks a genetic marker present at the corresponding locus from *L. sativa*, and (2) lacks a genetic marker genetically linked to the allele that confers adventitious shoots in *L. saligna* and/or comprises a genetic marker present at the corresponding locus from *L. sativa*; or (3) comprises a genetic marker genetically linked to the RBQ6 allele in *L. saligna* and/or lacks a genetic marker present at the corresponding locus from *L. sativa*, and (4) lacks a genetic marker genetically linked to the allele that confers reduced plant diameter or bubbled leaves in *L. saligna* and/or comprises a genetic marker present at the corresponding locus from *L. sativa*.

The method may further comprise detecting the allele(s) by a PCR-based method using oligonucleotide primer pair(s). In certain embodiments the LK1475 allele is detected using the primer pair comprising SEQ ID NO:1 and SEQ ID NO:2; the LE1276 allele is detected using the primer comprising SEQ ID NO:3 and SEQ ID NO:4; or the LE0350 allele is detected using the primer pair comprising SEQ ID NO:5 and SEQ ID NO:6. In other embodiments, the LE3118 allele is detected using the primer pair comprising SEQ ID NO:7 and SEQ ID NO:8, the LE9214 allele is detected using the primer pair comprising SEQ ID NO:9 and SEQ ID NO:10, or the LE0420 allele is detected using the primer pair comprising SEQ ID NO:11 and SEQ ID NO:12.

In alternative embodiments, the method may comprise selecting a progeny plant by detecting at least two alleles selected from the group consisting of: an LK1475 allele, an LE0142 allele, an LE1244 allele, an LE7003 allele, an LE1276 allele, an LE0350 allele, an LE1219 allele, an LE0115 allele, an LE0204 allele, an LE1211 allele, an LE0428 allele, an LE0420 allele, an LE9214 allele, an LE0017 allele, an LK1413 allele, and an LE3118 allele.

In another aspect, the invention provides a plant comprising a chromosomal segment comprising an allele conferring resistance to *Bremia lactucae*, wherein the segment lacks a second allele that confers a trait selected from the group consisting of adventitious shoots, reduced plant diameter and bubbled leaves, wherein a sample of seed comprising the chromosomal segment is deposited under ATCC Accession No. PTA-9045 or ATCC Accession No. PTA-9046.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 5 contains histogram plots of three traits: plant diameter, number of adventitious shoots, and bolting date, which vary in the 28 $F_2$ lines that had different homozygous recombinations in the BIL2.2 region.

FIG. 6 contains histogram plots of three traits: *B. lactucae* resistance, plant diameter, and leaf bubble score, which vary in the 36 $F_2$ lines that had different homozygous recombinations in the BIL6.3 region.

DETAILED DESCRIPTION OF THE INVENTION

Figure 1:
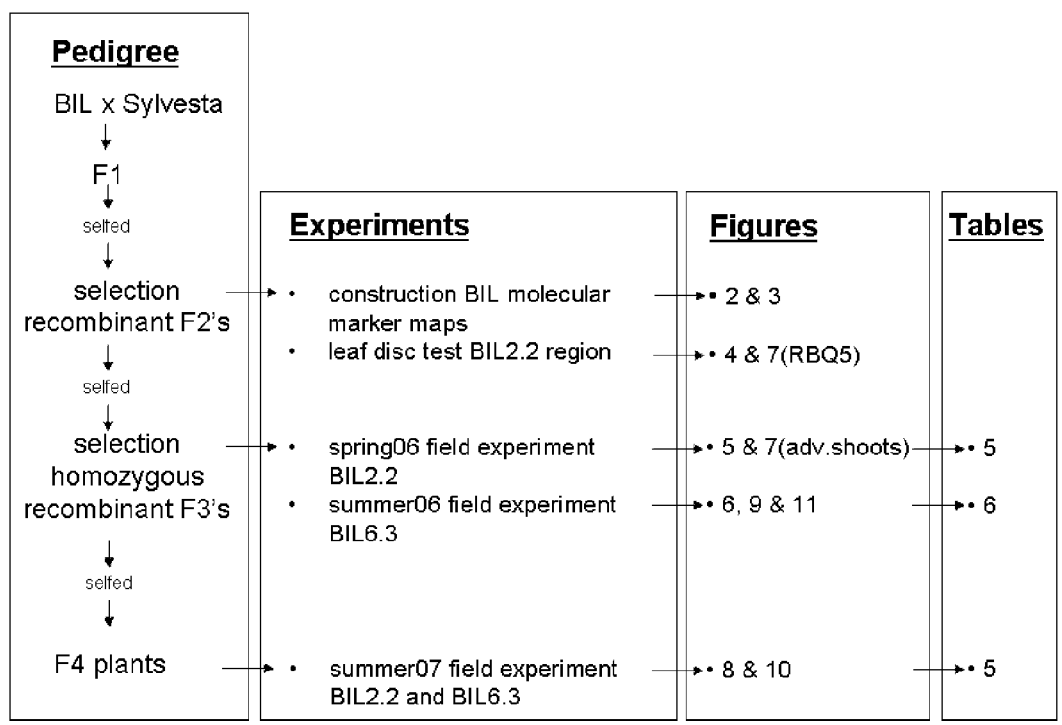
FIG. 1 depicts an overview of the pedigree for plant materials, used in different experiments which are linked to figures and tables.

The invention provides methods and compositions relating to plants, seeds and derivatives of lettuce (*L. sativa*) lines comprising introgressions from *L. saligna*, such that the lines comprising these reduced introgressions display quantitative resistance to *Bremia lactucae*, without also displaying undesirable agronomic traits such as adventitious shoots, reduced plant diameter, and bubbled leaf, that have previously been found to be transmitted with the quantitative Downy Mildew resistance trait. In certain embodiments, the invention relates to lettuce lines comprising reduced introgressions that retain RBQ5 and/or RBQ6 Downy Mildew resistance alleles lacking alleles derived from *L. saligna* that are associated with reduced plant diameter, adventitious shoots and/or bubbled leaves. In certain embodiments, parts of plants of such lines are also contemplated, including cells, embryos, seeds, roots, stems, leaves, flowers, and pollen.

Another aspect of the current invention concerns methods for obtaining a lettuce line comprising at least one reduced *L. saligna* introgression, wherein the lettuce plants display quantitative resistance to *Bremia lactucae*, but lack BIL2.2 and BIL6.3 QTL's that confer production of adventitious shoots or reduced plant diameter and/or bubbled leaves. In certain embodiments, methods for obtaining such plants comprise obtaining a *Lactuca* plant heterozygous for the RBQ5 and/or RBQ6 allele(s) from *L. saligna*, obtaining progeny from such a plant, and selecting one or more such progeny plants wherein genetic recombination has surprisingly occurred such that the progeny comprises an RBQ5 and/or RBQ6 allele, but does not comprise an allele that confers reduced plant diameter or production of adventitious shoots. In particular embodiments the method may comprise obtaining a progeny plant that comprises such allele(s) by identifying one or more genetic markers genetically linked to the RBQ5 and/or RBQ6 allele(s). Identifying the genetic markers may comprise a phenotypic, a genetic, or a biochemical test, and may include screening a parent and/or progeny plant for the presence of, for instance, one or more allele described herein, including, for example, a LK1475 allele from *L. saligna*, a LE0142 allele from *L. saligna*, a LE1244 allele from *L. saligna*, a LE7003 allele from *L. saligna*, a LE1276 allele from *L. saligna*, a LE0350 allele from *L. sativa*, a LE1219 allele from *L. sativa*, a LE0115 allele from *L. sativa*, a LE0204 allele from *L. sativa*, a LE3118 allele from *L. saligna*, a LK1413 allele from *L. saligna*, a LE0017 allele from *L. saligna*, a LE9214 allele from *L. saligna*, a LE0420 allele from *L. sativa*, a LE0428 allele from *L. sativa* and a LE1211 allele from *L. sativa*. In certain embodiments, one may screen for the presence of two or more genetic markers.

In certain embodiments, the method comprises identifying a lettuce plant comprising an *L. saligna*-derived introgression in linkage group 2, and mapping between, and including, LE1276 or LE7003; and LE0142 or LK1475; wherein the linkage group 2 sequence confers detectable resistance to *B. lactucae*, and lacking substantial growth of adventitious shoots. In a specific example, an average adventitious shoot score of ≤1 is observed according to such methods. In particular embodiments, the method comprises identifying a lettuce plant comprising *L. saligna* allele(s) at one or more of the following loci: LE1276, LE7003, LE1244, LE0142 and LK1475, and comprising *L. sativa* allele(s) at one or more of the following loci: LE0204, LE0115, LE1219, and LE0350 that exhibits *B. lactucae* resistance In other embodiments, the method may also comprise identifying a lettuce plant comprising an *L. saligna*-derived introgression in linkage group 6, mapping between loci LE0420 and LE3118, and including LK1413, LE0420, LE3118, LE0117, and LE9214, wherein the linkage group 6 sequence confers resistance to *Bremia lactucae*. In specific embodiments, a plant of the invention comprising resistance to *Bremia lactucae* lacks a second allele genetically linked to the allele conferring resistance wherein said second allele confers at least one trait selected from reduced plant diameter and bubbled leaves. Those of skill in the art will recognize that the expression of a trait such as resistance to *Bremia lactucae*, reduced plant diameter, and bubbled leaves can vary depending upon environmental conditions, but that such traits may be readily identified using head to head comparisons relative to other plants grown under the same or similar environment. In one embodiment, phenotypic trait values can be assigned, although the numbers are not absolutes given the aforementioned environmental influences and ability to make reliable head to head comparisons. Examples of such measurements include a *B. lactucae* resistance phenotype of less than about 2; a bubble leaf measurement of less than about 2.5; and a plant diameter of about 33 cm or greater. In other particular embodiments, the invention provides methods that comprise identifying a lettuce plant comprising an *L. saligna* allele at one or more of the following loci: LE9214, LE0017, LK1413; and an *L. sativa* allele at one or more of the following loci: LE1211, LE0428, LE0420, that exhibits resistance to *Bremia lactucae*. In one specific embodiment, such a plant comprises a *B. lactucae* resistance phenotype of ≤2, a bubble leaf measurement of ≤2.5, and a plant diameter of about 33 cm or greater. In a still further embodiment, a plant provided herein comprises an average adventitious shoot score of ≤1.

Exemplifying the inability to introduce quantitative resistance to *Bremia* into cultivated lettuce without undesirable effects are lines developed from an interspecific *L. sativa*×*L. saligna* cross. In these studies, *L. saligna* accession CGN05271, which contains quantitative resistance to *Bremia* was crossed with a susceptible cultivated *L. sativa* line, cv. 'Olof'. Repeated backcrossing to the Olof line, followed by selfing produced a series of backcross inbred lines (BILs) (Jeuken et al. 2004). RBQ5 and RBQ6 were resistance QTLs identified in this study, and are respectively found in BIL2.2 and BIL6.3. Despite a ten year study (Jeuken et al., 2001, Jeuken et al., 2002a, Jeuken et al., 2002b, Jeuken et al., 2004, Jeuken et al., 2008), lines could not be created that retained the disease resistance phenotype without horticultural defects, such as plant diameter, leaf bubbling, and adventitious shoots. This was the likely outcome, as most introgressions from wild relatives of domesticated species fail to result in commercially-acceptable varieties. This failure is often attributed to pleiotropy. It is obvious to speculate that an altered leaf, root morphology or other plant phenotype such as plant diameter could alter the pathogen's normal entry into the plant, and thus an undesirable agronomic trait would not be separable from a co-localized disease resistance trait.

Undesirable traits such as adventitious shoots, reduced plant diameter, and bubbled leaf were found to co-locate with desirable Downy Mildew resistance traits in the original BIL2.2 and BIL6.3 introgressions. The presence of these undesirable traits has hampered application of this quantitative resistance to lettuce breeding. However, the present invention demonstrates efficient screening for, and identification of, recombinant progeny lettuce plants and progeny that comprise a portion of the original introgressed region from *L. saligna* that confers disease resistance, while lacking *L. saligna* derived regions that specify QTL's for the undesirable traits.

Formation of a "reduced" introgression is understood to be caused by recombination event(s) in the vicinity of the RBQ5 or RBQ6 QTL(s). Lines comprising a reduced BIL2.2 and/or BIL6.3 introgression, i.e. which have undergone a recombination event close to the QTL specifying Downy Mildew resistance, may efficiently be screened by use of molecular and/or phenotypic markers. Thus, plant populations or progeny of such populations, segregating (i.e. heterozygous) with respect to the QTL's specified by the BIL2.2 and/or BIL6.3 introgressions, may be screened for plants having a recombinant phenotype, e.g. Downy Mildew resistance in combination with the lack of, for instance, a reduced plant diameter or adventitious shoots phenotype associated with the herein described *L. saligna* QTL(s).

Since *Lactuca saligna* (wild lettuce) is resistant to all downy mildew races and can be considered to be a non-host of the pathogen, *L. saligna* is an excellent source for genetically-based resistance to the downy mildew pathogen in lettuce. Multiple accessions of *L. saligna* (e.g. CGN05271, as well as CGN05327, LSA/92/1, etc.) are available, for instance from the Center for Genetic Resources (Wageningen, The Netherlands). Downy Mildew resistance of *L. saligna* may be non race-specific (e.g. Lebeda et al., 2002), and hence more durable than typical race-specific resistance.

Thus certain quantitative resistance loci (located within introgressions BIL2.2 or BIL6.3) were mapped for two *L. saligna* introgressions that confer Downy Mildew resistance in a butter head lettuce background (*L. sativa* cv. Olof and cv.

Sylvesta). Further, combinations of two or more reduced introgressions that specify quantitative Downy Mildew resistance, yet lack portions of these introgressions that specify undesirable agronomic traits, can result in substantial levels of Downy Mildew resistance, which would differ mechanistically from the qualitative resistance conferred by specific single resistance genes (e.g. Dm genes and R-genes) that operate via gene-for-gene interactions. Additionally, quantitative and qualitative sources of Downy Mildew resistance may be combined to further improve breeding prospects for *B. lactucae* resistance, while maintaining desired agronomic traits in cultivated lettuce. Thus, for instance, a lettuce line carrying one or more of RBQ5 and/or RBQ6 may be crossed with a lettuce line comprising, but not limited to, one or more R genes specifying qualitative resistance to *Bremia lactucae*, such as DM1-DM16 and R17-R40, among others.

A. BREEDING OF LETTUCE LINES DISPLAYING DOWNY MILDEW RESISTANCE

One aspect of the current invention concerns methods for crossing a lettuce line comprising reduced *L. saligna* introgression conferring quantitative Downy Mildew resistance with itself or a second plant and the seeds and plants produced by such methods. These methods can be used for production and propagation of cultivated lettuce lines displaying quantitative Downy Mildew resistance without agronomically undesirable traits that have previously associated with the resistance traits. The methods also can be used to produce hybrid lettuce seeds and the plants grown therefrom. Hybrid seeds are produced by crossing such lines with a second lettuce parent line.

Sources of Downy Mildew resistance are known in the art and may be used in accordance with certain embodiments of the invention. One such example is *Lactuca saligna* accession CGN05271, which can be obtained from the Center for Genetic Resources (Wageningen, The Netherlands). Other Downy Mildew resistance sources have also been described and are known in the art (see, for example, Lebeda et al., 1995; Bonnier et al., 1992; Gustafsson, 1989; Jeuken et al., 2002b; and Netzer, 1976).

In accordance with the invention, novel varieties may be created by crossing Downy Mildew resistant lines followed by generations of selection as desired and inbreeding for development of uniform lines. New varieties may also be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are typically involved.

Uniform lines of new varieties may also be developed by way of doubled-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a Downy Mildew resistant line of the present invention and progeny thereof to achieve a homozygous line.

Backcrossing can also be used to improve an inbred plant. Backcrossing transfers a specific desirable trait, such as Downy Mildew resistance, from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Lettuce varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many genetic improvement programs for lettuce are focused on morphology and horticultural performance including color, size, taste and head shape, as well as disease resistance/tolerance (e.g., viral, fungal and bacterial) and post-harvest problems (Ryder, 1986). Another objective is uniformity and earliness of head formation, thus improving yields. Since lettuce is grown in a variety of environments regarding soil, temperature, sun exposure and water quality, adaptation to those environments is another goal. Certain heat-induced trauma, such as thermal dormancy, premature bolting and tipburn, may also be targeted, in a breeding program, for development of lines displaying such tolerance or resistance.

As described above, a lettuce line of the present invention exhibits desirable agronomic traits, including quantitative Downy Mildew resistance, and improved average plant diameter (e.g. relative to *L. saligna*). These and other performance characteristics of such lines were analyzed relative to parental and sibling lines. Results of such an analysis are presented in Tables 5 and 6.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. Selection of lettuce plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes.

Procedures for marker assisted selection are of particular utility for introgression of given traits. Types of genetic markers that could be used in accordance with the invention include, but are not necessarily limited to, Simple Sequence Length Polymorphisms (SSLPs) (Williams et al., 1990), Cleaved Amplified Polymorphic Sequences (CAPs) (e.g. Konieczny and Ausubel, 1993), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

B. PLANTS DERIVED FROM A LETTUCE LINE OF THE PRESENT INVENTION BY GENETIC ENGINEERING

Many useful traits that can be introduced by backcrossing, as well as directly into a plant, are those which may be introduced by genetic transformation techniques. Genetic transformation may therefore be used to insert a selected transgene into the lettuce line of the invention or may, alternatively, be used for the preparation of transgenes which can be introduced by backcrossing. Methods for the transformation of plants, including lettuce, are well known to those of skill in the art.

Vectors used for the transformation of lettuce cells are not limited so long as the vector can express an inserted DNA in the cells. For example, vectors comprising promoters for constitutive gene expression in lettuce cells (e.g., cauliflower mosaic virus 35S promoter) and promoters inducible by exogenous stimuli can be used. Examples of suitable vectors include pBI binary vector. The "lettuce cell" into which the vector is to be introduced includes various forms of lettuce cells, such as cultured cell suspensions, protoplasts, leaf sections, and callus.

A vector can be introduced into lettuce cells by known methods, such as the polyethylene glycol method, polycation method, electroporation, *Agrobacterium*-mediated transfer, particle bombardment and direct DNA uptake by protoplasts. See, e.g., Pang et al. (1996).

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner. An example of electroporation of lettuce protoplasts is presented in Chupeau et al. (1989).

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics® Particle Delivery System, which can be used to propel particles coated with DNA or cells through a screen, such as a stainless steel or NYTEX screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples involving microprojectile bombardment transformation with lettuce can be found in, for example, Elliott et al. (2004) and Molinier et al. (2002).

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium* (and other *Rhizobia*), allowing for convenient manipulations (Klee et al., 1985; Broothaerts et al., 2005). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055). For example, U.S. Pat. No. 5,349,124 describes a method of transforming lettuce plant cells using *Agrobacterium*-mediated transformation. By inserting a chimeric gene having a DNA coding sequence encoding for the full-length B.t. toxin protein that expresses a protein toxic toward Lepidopteran larvae, this methodology resulted in lettuce having resistance to such insects.

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994) and Ellul et al. (2003).

A number of promoters have utility for plant gene expression for any gene of interest including but not limited to selectable markers, scorable markers, genes for pest tolerance, disease resistance, nutritional enhancements and any other gene of agronomic interest. Examples of constitutive promoters useful for lettuce plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the lettuce lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a lettuce plant according to the invention. Non-limiting examples of particular genes and corresponding phenotypes one may choose to introduce into a lettuce plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

C. ORIGIN AND BREEDING HISTORY

Parent designation 50070045 (F5 generation) was derived by repeated selfing, following crossing of *L. sativa* cv. Sylvesta with a backcross inbred line (BIL) derived from a cross of *L. saligna* CGN05271 with *L. sativa* cv. Olof (Jeuken, 2004), wherein genetic markers denoting the described recombination at RBQ5 were selected for. Designation 50066390 (F3 generation) was derived by repeated selfing, following crossing of *L. sativa* cv. Sylvesta with a backcross inbred line (BIL) derived from a cross of *L. saligna* CGN05271 with *L. sativa* cv. Olof (Jeuken, 2004), with selection for genetic markers denoting the described recombination at RBQ6. Samples of seeds of 50066390 and 50070045 have been deposited with the ATCC under Accession Nos. PTA-9045 and PTA-9046, respectively.

D. DEFINITIONS

In the description and tables herein, a number of terms are used. In order to provide a clear and consistent understanding of the specification and claims, the following definitions are provided:

Adventitious shoots score: A count of the average number of shoots arising from secondary (i.e. non-apical) buds.

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Bubble leaf score: A count of the average rating for the bubble leaf phenotype based on a scale of 1-5, wherein 1 refers to almost flat leaves such as typically found with cv. Sylvesta, while 5 refers to highly bubbled leaves as found in lines comprising BIL6.3. Measurement was done at about 47 days after planting.

Cultivated lettuce: Lettuce which is suitable for consumption and meets the requirements for commercial cultivation, e.g. typically classified as *Lactuca sativa*. In addition to the lettuce plants themselves, and the parts thereof suitable for consumption, such as the heads or leaves, the invention comprises parts or derivatives of the plant suitable for propagation. Examples of parts suitable for propagation are organ tissues, such as leaves, stems, roots, shoots and the like, protoplasts, somatic embryos, anthers, petioles, cells in culture and the like. Derivatives suitable for propagation are for instance seeds. The plants according to the invention can be cultivated or propagated in the conventional manner but also by means of tissue culture techniques from plant parts.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in co-dominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Recombination event is understood to mean a meiotic crossing-over.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a lettuce variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a lettuce plant by transformation.

Triploid: A cell or organism having three sets of chromosomes.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

E. DEPOSIT INFORMATION

A deposit was made of at least 2500 seeds of lettuce designation 50070045, which comprise a RBQ5 allele of *Lactuca saligna* conferring quantitative resistance to *Bremia lactucae* and lacks an allele that is genetically linked to the RBQ5 allele in *Lactuca saligna* and confers adventitious shoots. A deposit was also made of at least 2500 seeds of designation 50066390 containing a RBQ6 allele of *Lactuca saligna* conferring quantitative resistance to *Bremia lactucae* and lacking an allele genetically linked to the RBQ6 allele in *Lactuca saligna* that confers reduced plant diameter or bubbled leaves. The deposits were made with the American Type Culture Collection (ATCC), 10801 University Boulevard, Manassas, Va. 20110-2209 USA. The deposits are assigned ATCC Accession Nos. PTA-9046, and PTA-9045, respectively. The date of deposit was Mar. 13, 2008. Access to the deposits will be available during the pendency of the application to persons entitled thereto upon request. The deposits will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

Example 1

Creation of Recombinant Lines and Genetic Marker Mapping

Backcross inbred lines (BILs) with introgressions from *Lactuca saligna* accession CGN05271 were produced with repeated backcrossing to an *L. sativa* parental line named Olof (Jeuken et al., 2004). Wild accessions of the *Lactuca* family, including accession CGN05271, can be obtained from the Center for Genetic Resources (Wageningen, The Netherlands). BILs 2.2 and 6.3 were identified having introgressions from *L. saligna* in regions of linkage groups (LGs) 2 and 6, respectively, conferring quantitative resistance to Downy Mildew (Jeuken et al., 2008, here after referred to as LG 2 region and LG 6 region).

To precisely map the *Bremia* resistance and horticultural traits in the LG 2 and 6 regions, these BILs were each crossed to the cultivated variety Sylvesta, and the $F_1$ plants were self-pollinated to produce two $F_2$ populations, one population each for the LG 2 and LG 6 regions (FIG. 1) FIG. 1 displays the pedigree used, where different generations were tested throughout the examples, and where those results are presented within the examples. Expressed Sequence Tagged sequences were retrieved from the University of California Compositae Genome Project Database (Davis, Calif.), and used to create molecular markers using standard techniques well known in the art. Positions were compared with those of previously identified markers in the general vicinity of BIL2.2 and BIL 6.3, respectively on linkage groups 2 and 8 Linkage group 6 of Jeuken et al., 2001 is homologous to linkage group 8 in the University of California Compositae Genome Project Database (Davis, Calif.). Alleles derived from *L. sativa* and *L. saligna* were detected using a Polymerase Chain Reaction-(PCR) based methods (i.e. using DNA sequence length polymorphisms, or using Cleaved Amplified Polymorphisms; Konieczny and Ausubel, 1993). All PCR reactions contained 2.0 microliters 10×PCR buffer (Invitrogen, Paisley, UK), 0.8 microliters 50 mM $MgCl_2$, 0.8 microliters of a stock solution containing 2.5 mM of each dNTP, 0.4 microliters 10 μM PCR primer A, 0.4 microliters 10 μM primer B, 0.1 microliters Taq polymerase (Invitrogen, Paisley, UK, catalog #10342-020), 1.0 microliters DNA (about 10-100 ng) and 14.5 microliters sterile water. PCR reaction conditions for markers used to precisely map the LG 2 and LG 6 regions are described in Tables 1 and 2, respectively.

TABLE 1

PCR reaction conditions for BIL2.2 mapping.

| Denaturation Step | Cycling | Primer Extension Step | Hold Step |
|---|---|---|---|
| 2 minutes at 94° C. | 40x: 1 min at 92° C./ 1 min at 52° C./2 min at 72° C. | 30 min at 72° C. | 25° C. |

TABLE 2

PCR reaction conditions for BIL6.3 mapping.

| Denaturation Step | Cycling | Primer Extension Step | Hold Step |
|---|---|---|---|
| 2 minutes at 94° C. | 40x: 1 min at 92° C./ 1 min at 60° C./2 min at 72° C. | 5 min at 72° C. | 25° C. |

Tables 3 and 4 provide information for the PCR assays for markers in the LG 2 and LG 6 regions, respectively. Each table lists the primer sequences and their SEQ ID numbers, the enzyme used post-PCR to reveal the fragment-length polymorphism (if necessary), and the approximate DNA fragment lengths expected from *L. sativa* and *L. saligna*. Enzyme digestion conditions followed the manufacturer's recommendations, and fragments were resolved using agarose gel electrophoresis. No sequence polymorphisms were observed using these assays between the *L. sativa* cultivars Olof and Sylvesta.

TABLE 3

Details for PCR primers and allele detection of markers in the LG 2 region.

| | LK1475 | LE1276 | LE0350 |
|---|---|---|---|
| Primer 1 (SEQ ID #) | GGAGTTCAGGGCCTCTGTC (1) | TTTGGGTTCCTTCAGTTTGC (3) | CGGTTGCTCAAGACCTCTCA (5) |
| Primer 2 (SEQ ID #) | CCGATTCTGCGGTTATCTTC (2) | CACAGTTTGGGATGAACACG (4) | AGCGAACGACCCTCTAACG (6) |
| Enzyme | none | none | MboI |
| *L. sativa* DNA fragments produced | 700 base pairs | 200 base pairs | 375 base pairs |
| *L. saligna* DNA fragments produced | 550 base pairs | 220 base pairs | 300 and 75 base pairs |

TABLE 4

Details for PCR primers and allele detection of markers in the LG 6 region.

| | LE3118 | LE9214 | LE0420 |
|---|---|---|---|
| Primer 1 (SEQ ID #) | GGAGGTTCATGGCCTACTTTAC (7) | CGTTGACAACCACTCACCAC (9) | GAAACCAGAGGAGGCAGTTG (11) |
| Primer 2 (SEQ ID #) | GGCTCAATGACTGACACTTGC (8) | ACTGAAGTTTTTGGCGAAGC (10) | GTGCTGCTTCTTACAACCAAAC (12) |
| Enzyme | HinfI | RsaI | ScrFI |
| *L. sativa* DNA fragments produced | 280, 180, 150 and 100 base pairs | 400, 350 and 250 base pairs | 310 and 200 base pairs |
| *L. saligna* DNA fragments produced | 350, 180, 100 and 70 base pairs | 1,000 base pairs | 280 and 230 base pairs |

Figure 2:
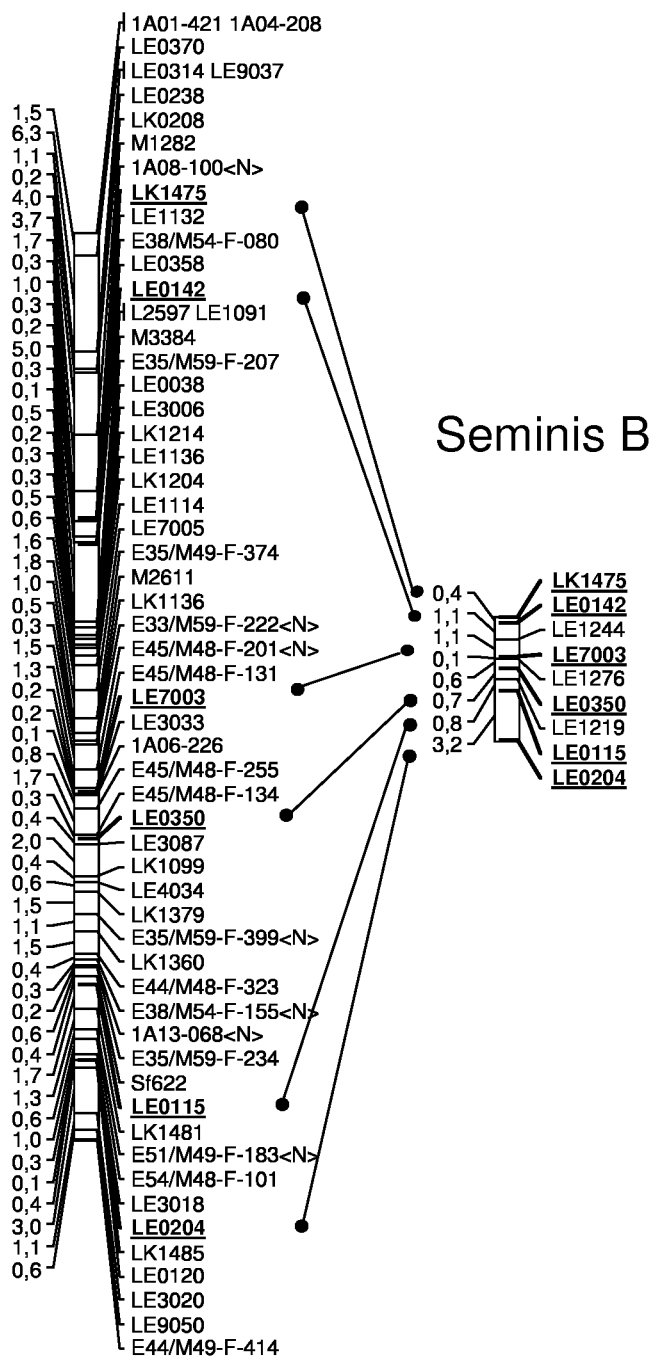
FIG. 2 depicts on the left, a relevant part of the molecular marker map from *Lactuca* linkage group 2 referred to as Michelmore LG2. On the right is a molecular marker map of the Backcross Inbred Line (BIL) 2.2, referred to as Seminis BIL2.2, displaying the region introgressed from *L. saligna* that contains both the favorable trait (disease resistance) and unfavorable trait (adventitious shoot phenotype). Each map is formatted with the interval lengths between the markers in centiMorgans (cM) to the left, and the marker names to the right of the maps. Common markers between maps are underlined and bold and corresponding positions of these markers are indicated with the symbol ●—●..

Two flanking markers, LE0204 and LK1475, were scored on 699 $F_2$ plants (FIG. 1) derived from BIL2.2×*L. sativa* cv. Sylvesta. Recombinants plants were screened with nine molecular markers, including the three diagnostic markers in Table 3. Using JOINMAP software (Van Ooijen and Voorips, 2001), with the Kosambi mapping function, the LG 2 region was finely mapped, with an average chi-square value of 0.054. FIG. 2 compares the fine mapping results with the publicly available map for LG 2. Corresponding marker positions on the maps note that the fine map of LG 2 is shorter than the publicly available map; this discrepancy maybe attributed to double recombinants in the introgression area, or due to scoring errors in the publicly available map. Recombinations may also occur less frequently in the introgressed region.

Figure 3:
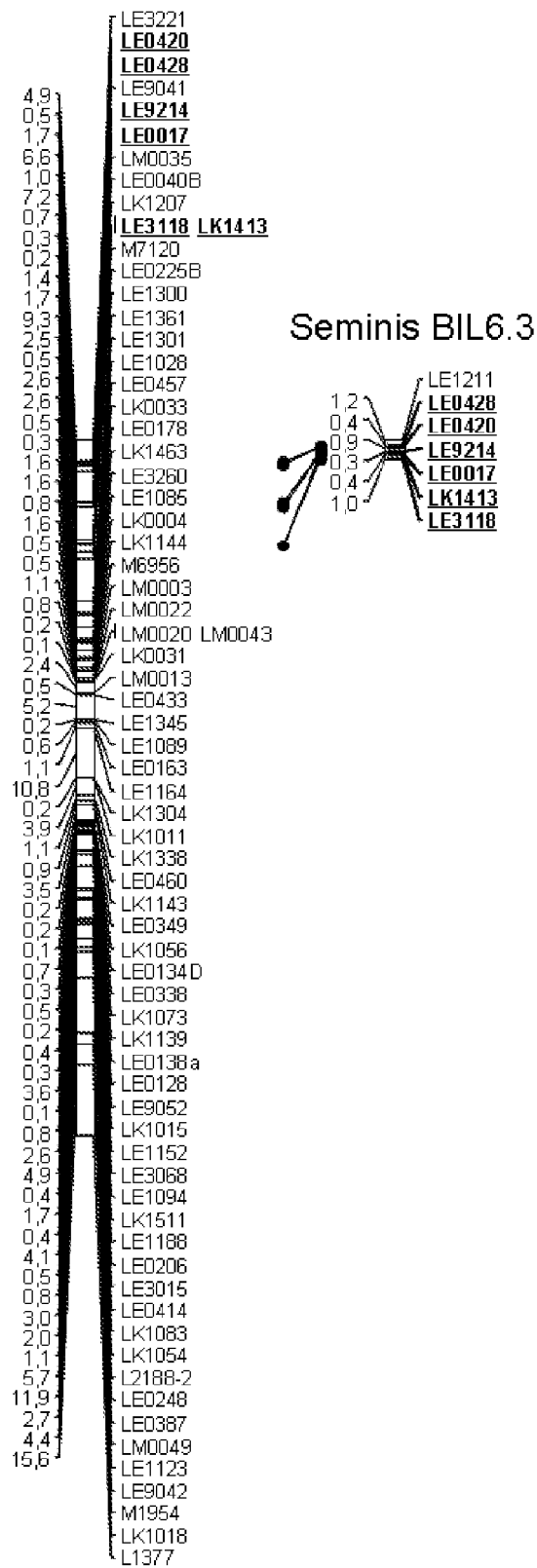
FIG. 3 depicts on the left a molecular marker map from *Lactuca* linkage group 8 referred to as Michelmore_LG8. On the right is a molecular marker map of the Backcross Inbred Line 6.3, referred to as Seminis_BIL6.3 displaying the region introgressed from *L. saligna* that contains both the favorable trait (disease resistance) and unfavorable traits (plant diameter and leaf bubbling). Each map is formatted with the interval lengths between the markers in centiMorgans (cM) to the left, and the marker names to the right of the maps. Markers in common between maps are underlined and bold and corresponding positions of these markers are indicated with the symbol ●—●..

Seven markers, including the diagnostic markers in Table 4, were scored on 556 $F_2$ plants (FIG. 1) derived from BIL6.3×*L. sativa* cv. Sylvesta. Using JOINMAP software (Van Ooijen and Voorips, 2001), with the Kosambi mapping function, the LG 6 region was finely mapped with an average chi-square value of 0.026. FIG. 3 compares the fine mapping results with the homologous publicly available map for LG 8 in the University of California Compositae Genome Project Database (Davis, Calif.) Like the comparison above for the LG 2 region, the corresponding marker positions on the maps reveal that the LG 6 fine map is shorter than publicly available map; this discrepancy maybe attributed to double recombinants in the introgression area, or due to scoring errors in the publicly available map. Recombinations may also occur less frequently in the introgressed region.

Example 2

Disease, Leaf Bubbling, Plant Diameter, and Adventitious Shoot Phenotyping

Figure 4:
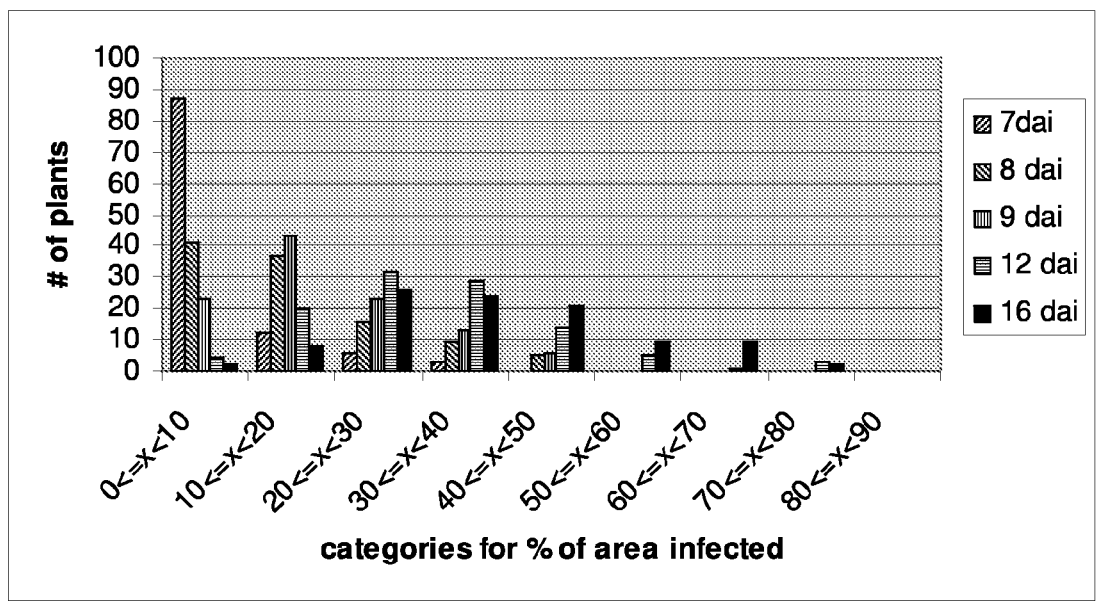
FIG. 4 depicts a histogram that plots the average *B. lactucae* infection, measured by the percentage of leaf area displaying foliar disease symptoms. Averages were from four leaf disks per $F_2$ plant. Leaf disks of 107 $F_2$ plants were measured over time, and averages per plant are partitioned into 8 categories. The categories are 10% increasing steps of leaf area infected. The plants tested were $F_2$ recombinants in the BIL2.2 area. These leaf disks were scored at 7-9, 12 and 16 days after inoculation (dai).

Disease: *Bremia* disease was monitored either using a leaf disk test, or field screening using naturally-occurring *Bremia*. Leaf disk tests were performed on 107 greenhouse-grown $F_2$ plants that were selected for recombination in the BIL2.2 region based on markers as described in example 1. Parent lines and check cultivars also were included in the test. Inoculum was produced by multiplying the *B. lactucae* isolate BL21 on approximately 7 day-old plants of *L. sativa* cv. Prado, a susceptible variety. 7-10 day old sporangiospores were washed from the leaves with autoclaved tap water. The suspension was sieved and the spores were counted. A concentration of 10,000 spores per ml was utilized. The official NAKT (Naktuinbouw; Netherlands Inspection Service for Horticulture) host range was used to check the race of the *B. lactucae* isolate. Two to four leaf disks of 2.5 cm diameter were used from each plant, placed on wet filter paper, and inoculated with a *B. lactucae* (BL21) spore suspension, and incubated under high humidity in a planting box at 15° C. with 9 hours of light per day. After 7, 8, 9, 12, and 16 days, the percentage of infected area covered by *B. lactucae* sporangiospores was estimated. Using this method, FIG. 4 shows a histogram of the disease responses for $F_2$ plants, recombinant in the BIL2.2 region.

Field tests were performed on $F_3$ plants that were selected for being homozygous recombinant in the LG 2 or LG 6 regions using markers described in example 1, or on the $F_4$ plants derived form these $F_3$ plants. These field tests relied on naturally occurring *Bremia* disease pressure. Plants were rated at 30, 37 and 43 days after transplanting using a 1 to 9 disease rating scale, wherein the higher the rating score, the greater the susceptibility as described below for the third field test.

Detailed description for every class of the disease scale of *B. lactucae* on *Lactuca* plants:
1: no infection
2: 1-2 spots
3: 3-5 spots
4: 6-7 spots
5: 8-9 spots
6: 10-12 spots
7: big spots
8: big regions covered
9: completely covered Plant diameter: Plant diameter was measured in field grown plants of the recombinant $F_3$ or $F_4$ plants, between 40 and 44 days after transplanting. Plant diameter is the length between the longest leaves on both sides of the plant.

Leaf bubbling: Leaf bubbling was measured on field grown recombinant $F_3$ plants 47 days after transplanting, using a rating scale of 1 (fewest bubbles) to 5 (most bubbles) as described below for the first and third field tests.

Adventitious shoots: The numbers of adventitious shoots were counted on recombinant $F_3$ plants growing in the field, 47 days after transplanting. Adventitious shoots were counted by looking from above.

Bolting date: The average bolting date was monitored using field grown plants of the recombinant $F_3$ plants. Data were scored after 40 days. Therefore, bolting date scores of 5 and 15 reflect plants that bolted 45 and 60 days after transplanting.

Three different field tests were conducted on the recombinant $F_3$ or $F_4$ plants, and each test included parents and check cultivars. The first field test was conducted in spring 2006 using 3 to 32 homozygous recombinant plants per $F_2$ line. Each of the 28 $F_2$ lines were derived from single BIL2.2 recombinant $F_2$ plants. The numbers of adventitious shoots were counted. There was no *Bremia* disease during this test. The number of plant per $F_2$ line was variable due to available number of seeds and the number of homozygous recombinants. Due to variation in number of plants no specific design has been used.

The second field test was conducted in fall 2006 using 2 to 20 homozygous recombinant plants per $F_2$ line, each derived from 36 BIL6.3 recombinant $F_2$ plants. *Bremia* field screening relied on natural disease pressure, and plants were scored using a 1 to 9 scale. The recombinants are scored relative to the parental scores, and the means are reported with the standard deviations displayed parenthetically (Table 6). For each recombinant plant diameter and bubbling were measured. Degree of leaf bubbles was measured by scoring relative to the parental scores (Sylvesta=1, Olof=3 and BIL6.3=5) and the means are reported with the standard deviations displayed parenthetically (Table 6).

The third field test was conducted in fall 2007 in a randomized complete-block design with 6 blocks and 6 plants per line. The *Bremia* resistance trait was scored by using the absolute 1-9 scale. On the 15 $F_3$ lines, recombinant for the LG 6 region, leaf bubbles and plant diameter were measured Adventitious shoots, on the 28 lines recombinant for the LG 2, could not be measured because the growing season was shortened due to an early frost. No significant QTL was seen for Leaf bubbles at LG6 in 2007.

FIGS. 5 and 6 demonstrate the phenotypic variation observed for disease, plant diameter, adventitious shoot, bolting date and leaf bubbling traits. These demonstrate the varying nature of these quantitative traits.

Example 3

Fine Mapping Traits and Characterization of Recombinants in the LG 2 Region

Figure 7:
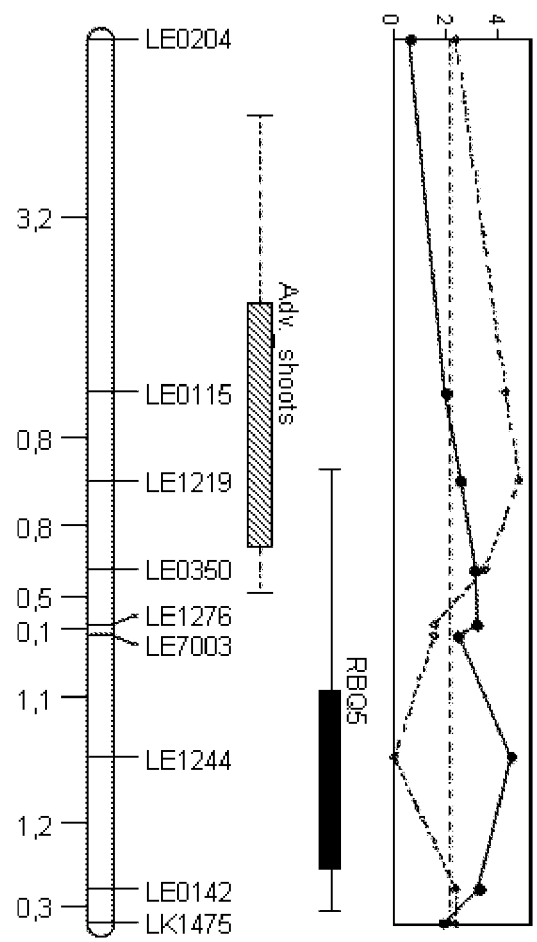
FIG. 7 depicts QTL mapping results for adventitious shoots from 28 homozygous recombinant $F_2$ lines and QTL mapping results for *B. lactucae* resistance (QTL referred to as RBQ5) from leaf disk tests of 107 recombinant $F_2$ plants. Plant material was derived from the *L. sativa* cv. Sylvesta× BIL2.2 population. On the left is an expanded portion of the BIL2.2 map shown in FIG. 2. Marker positions are to the right of the map, and the map interval lengths between the markers are to the left of the map; these are shown in centiMorgans (cM). The boxed region to the right shows the significance level for the two traits, expressed as LOD score compared with the significance threshold, around a LOD score of 2, which was calculated with a permutation test. The threshold is shown using a dashed vertical straight line, while the trait scores vary according to the map position and are represented with a solid line for disease resistance and a dotted line for the adventitious shoot phenotype. Between the map and boxed are noted where the areas where the traits are located. These areas are noted with shorter thick and longer thin regions. The thick areas display the regions contained within 1 LOD unit of the highest LOD score. Similarly, the thin areas show the areas contained within 2 LOD units of the highest LOD score. The disease resistance QTL area, RBQ5, is shown with a solid line, and filled box, respectively for the 1 and 2 LOD steps, while the similar significant areas for the adventitious shoot trait are shown with a dotted line and hashed box.

High resolution map positions of QTL for *Bremia* resistance and adventitious shoots in the LG 2 region were determined by analyzing marker genotype data and phenotypic data with Interval QTL mapping using MapQTL® 4.0 (Van Ooijen et al., 2002). In FIG. 7, *Bremia* resistance data came from the leaf disc test on $F_2$ recombinants and the adventitious shoot data came from the first field test on homozygous recombined $F_3$ plants.

The expectation based on coincidence of these traits in the BIL lines was that the two QTLs would map to the same position. However, our data from the fine map indicate these two QTL map to different positions on LG 2 (FIG. 7). The distinct positions of these QTL are supported by the non-overlapping confidence intervals (thick solid and diagonally striped lines in FIG. 6), and these QTL positions can be described with respect to the map position of the markers. Marker LE1244 was found to map to the RBQ5 QTL, while markers LE0115 and LE1219 mapped to the adventitious shoots QTL. Markers LE0204 and LK1475 flank the two QTL. Additionally, markers LE0350, LE1276, and LE7003 map between the two QTLs.

Figure 8:
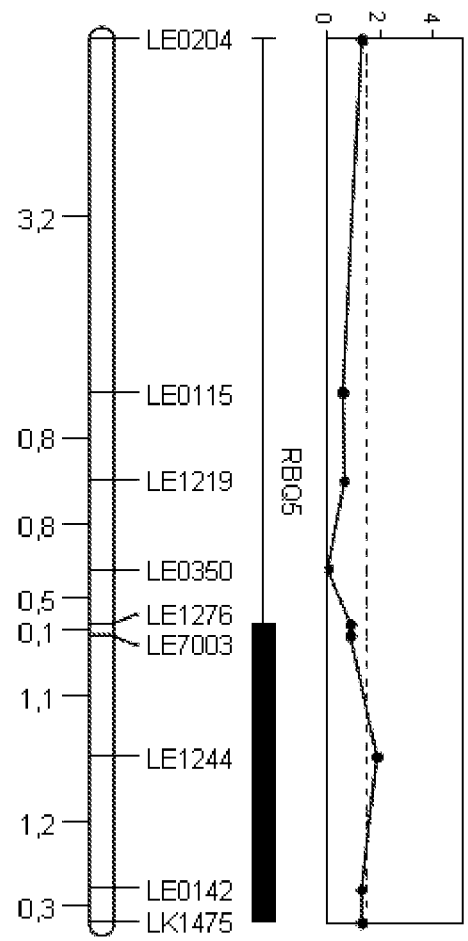
FIG. 8 depicts QTL mapping of 28 $F_3$ lines from the *L. sativa* cv. Sylvesta×BIL2.2 population for RBQ5 resistance on the map provided in FIG. 2. Lines are $F_4$ plants with reduced homozygous BIL2.2 introgressions. The resistance QTL is based on field observations of symptoms under natural disease pressure in summer 2007. Field observations are averaged data of scores of 36 plants for each line at three dates (30, 37 and 43 days after transplanting). Positions of markers are indicated and interval lengths (in cM) are on the left side of the linkage group. To the right of the linkage groups, is a box with the LOD plot from interval mapping: solid line for the *B. lactucae* resistance trait. The straight dotted line at about LOD=1.5 in the plot is the significance threshold calculated with a permutation test. The vertical bar with "RBQ5" represents the 1-LOD drop (fat bar) and the 2-LOD drop (thin bar) intervals.

The map position of the RBQ5 QTL was confirmed based on results from the third field test, in which *Bremia* disease symptoms were measured on the LG 2 recombinant $F_3$ lines under conditions of natural infection. These disease data were analyzed along with marker data as described above to provide a high resolution map position for the *Bremia* resistance under field conditions (FIG. 8). The results were very similar to the results from the leaf disc test, showing that marker LE1244 maps to the center of the one LOD confidence interval. Thus, the RBQ5 QTL, whether measured in the leaf disc test or field test, is in a different map position than the adventitious shoot QTL.

The high resolution mapping results allowed for molecular identification of progeny plants that have recombined between the QTL for *Bremia* resistance and the QTL for adventitious shoots on LG 2. These molecularly identified homozygous recombinants have phenotypic characteristics that concur with the molecular data. Examples of desirable recombinant lines that have the *L. saligna* marker alleles in the RBQ5 region and *L. sativa* marker alleles in the adventitious shoot QTL region are shown in Table 5. These lines have the higher disease resistance from *L. saligna*, and they have low numbers of adventitious shoot derived from *L. sativa*.

TABLE 5

Characterization of recombinant lines in the LG 2 region that have retained the higher *Bremia* resistance from *L. saligna*, but have eliminated the defects in adventitious shoots.

| | Phenotypes | | Genotypes[1] | | | | | | | | |
|---|---|---|---|---|---|---|---|---|---|---|---|
| Lines[2] | Adventitious shoots[3] | Resistance[4] | LK1475 | LE0142 | LE1244 | LE7003 | LE1276 | LE0350 | LE1219 | LE0115 | LE0204 |
| Olof | 0.0 (0.0) | 5.44 (0.78) | C | C | C | C | C | C | C | C | C |
| Sylvesta | 0.0 (0.0) | 6.75 (0.45) | C | C | C | C | C | C | C | C | C |
| BIL2.2 | 5.0 (2.59) | 3.38 (0.81) | D | D | D | D | D | D | D | D | D |
| Q510F4 | 0.10 (0.31) | 4.50 (1.05) | D | D | D | D | D | C | C | C | C |
| Q58F2 | 0.19 (0.68) | 4.67 (0.52) | D | D | D | D | D | C | C | C | C |

[1]Genotypes are scored with a 'D', indicating the presence of the donor (*L. saligna*) allele, or with a 'C', indicating the presence of the cultivated lettuce (*L. sativa*) allele. These genotypes are provided for 9 loci (LK1475, LE0142, LE1244, LE7003, LE1276, LE0350, LE1219, LE0115, and LE0204), that are contiguous on lettuce linkage group 2 (see FIGS. 2, 7 and 8). Protocols for molecular marker assays are found in example 1.
[2]Olof and Sylvesta are cultivated *L. sativa* lines that are susceptible to *Bremia*, but do not display the undesirable adventitious shoot trait. BIL2.2. contains the *Bremia* resistance QTL RBQ5. Lines Q510F4 and Q58F2 are recombinant lines derived from an original BIL2.2 x Sylvesta cross. These lines retain the RBQ5 *Bremia* resistance QTL, but do not suffer from the adventitious shoot horticultural defect.
[3]Adventitious shoots was measured as described in example 2. Means and standard deviations are reported, with the standard deviations displayed parenthetically.
[4]*Bremia* resistance was measured in the third field test as described in example 2. Plants were scored using a 1 (resistant) to 9 (susceptible) scale. Means and standard deviations are reported, with the standard deviations displayed in parentheses.

Example 4

Fine Mapping Traits and Characterization of Recombinants in the LG 6 Region

Figure 9:
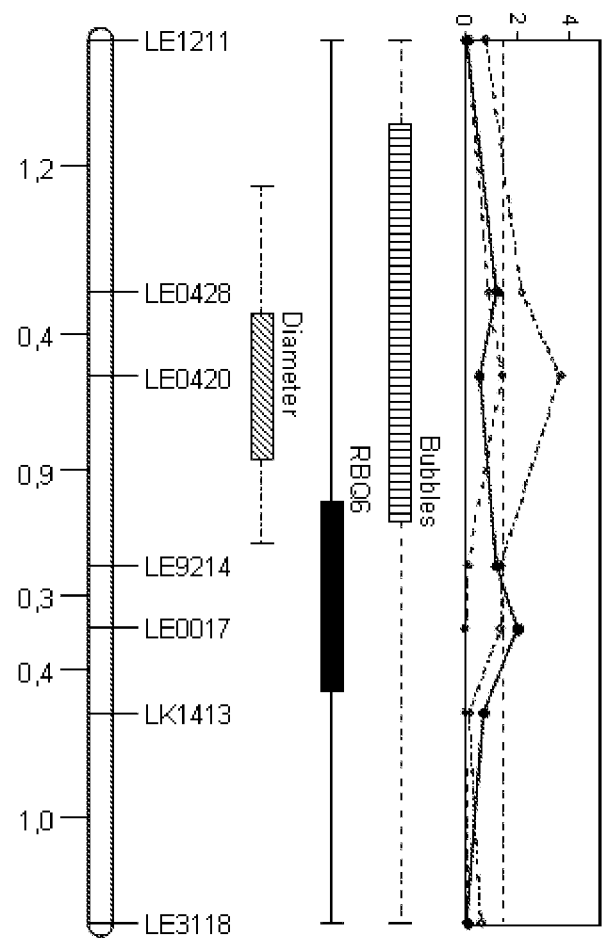
FIG. 9 depicts QTL mapping results from the *L. sativa* cv. Sylvesta×BIL6.3 population. The $F_2$ lines used to map plant head diameter, leaf bubbles and for *B. lactucae* resistance (QTL referred to as RBQ6) were homozygous recombinant $F_3$ plants in the BIL6.3 region. On the left is an expanded portion of the BIL6.3 map shown in FIG. 3. Marker positions are to the right of the map, and the map interval lengths between the markers are to the left of the map; these are shown in centiMorgans (cM). The boxed region to the right shows the significance level for the three traits, expressed as LOD score compared with the significance threshold, which was calculated with a permutation test. The threshold is shown using a dashed vertical straight line, while the trait scores vary according to the map position and are represented with a solid line for disease resistance, a dotted line for the plant diameter phenotype and a dashed line for the bubbled leaf phenotype. Between the map and boxed region the areas where the traits are located is noted. These areas are noted with shorter thick and longer thin regions. The thick areas display the regions contained within 1 LOD unit of the highest LOD score. Similarly, the thin areas show the areas contained within 2 LOD units of the highest LOD score. The disease resistance QTL area, RBQ6, is shown with a solid line, and filled box, respectively for the 1 and 2 LOD steps, while the similar areas for the plant diameter trait are shown with a dotted line and diagonal hashed box and areas for the bubbled leaf trait with dashed line and horizontally hashed box.

High resolution map positions of QTL for *Bremia* resistance, plant diameter and leaf bubbles in the LG 6 region were determined by analyzing marker genotype data and phenotypic data for lines that were homozygous recombinant in this region. The data for all three traits came from the second field test in summer 2006. These data were analyzed as described in example 3. As in example 3, our expectation, based on coincidence of these traits in the BIL lines, was that all three QTL would map to the same position. The expectation was met for the two horticultural traits, plant diameter and leaf bubbles. The one LOD confidence interval for plant diameter was within the one LOD confidence interval for leaf bubbling (FIG. 9), indicating that these two traits could not be separated with the resolution of our mapping, either because they are very tightly linked or controlled by a single locus with pleiotropic effects. However, our expectation was not met for the disease resistance trait with respect to the horticultural traits. The one LOD confidence interval for RBQ6 is non-overlapping or mostly non-overlapping with the two horticultural traits plant diameter and leaf bubbles (FIG. 9). These QTL positions can be described with respect to the map position of analyzed markers. Markers LE9214 and LE0017 were found to map to the RBQ6 QTL, while marker LE0420 mapped to the reduced plant diameter QTL and markers LE0420 and LE0428 map to the leaf bubbles QTL. Additionally, markers LE1211, LK1413, and LE3118 flank the three QTL's.

Figure 10:
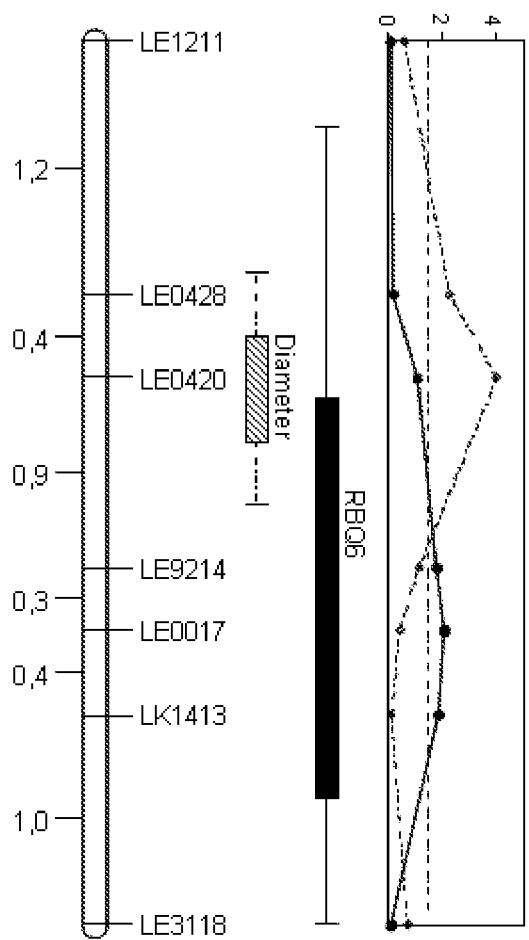
FIG. 10 depicts results of QTL mapping in the year subsequent to that in which data in FIG. 6 was obtained using 15 $F_3$ lines from the *L. sativa* cv. Sylvesta×BIL6.3 population for RBQ6 resistance on the map provided in FIG. 3. Lines are $F_4$ plants with reduced BIL6.3 introgressions. The QTLs are based on field observations in summer 2007. Disease field observations, under natural disease pressure, are averaged data of scores of 36 plants for each line at three dates (30, 37 and 43 days after transplanting). Diameter field observations are averaged data of scores of 36 plants for each line at 43 days after transplanting. Positions of markers are indicated and interval lengths (in cM) are on the left side of the linkage group. To the right of the linkage groups, is a box with the LOD plot from interval mapping: dashed line for plant diameter and solid line for the *B. lactucae* resistance trait. The straight dashed line in the LOD plot is the significance threshold calculated with a permutation test. QTL's which are significant are represented by vertical bars: the fat bar represents the 1-LOD drop interval and the thin bar represents the 2-LOD drop interval.

The map positions of the RBQ6 and plant diameter QTL were confirmed based on results from the third field test in summer 2007 in which *Bremia* resistance and plant diameter were measured for LG 6 recombinant $F_3$ lines. These trait data were analyzed along with marker data as described above to provide another estimate of high resolution map positions for QTL controlling these traits (FIG. 10). Although the one LOD confidence interval for the RBQ6 QTL was broader for this field test compared to the second field test (perhaps due to more variation in the pathogen test), the results were very similar to the results from second field test, showing that markers LE9214 and LE0017 map to the RBQ6 QTL, and marker LE0420 maps to the plant diameter QTL. These results support the conclusion that the RBQ6 and plant diameter QTL are located at different map positions.

Figure 11:
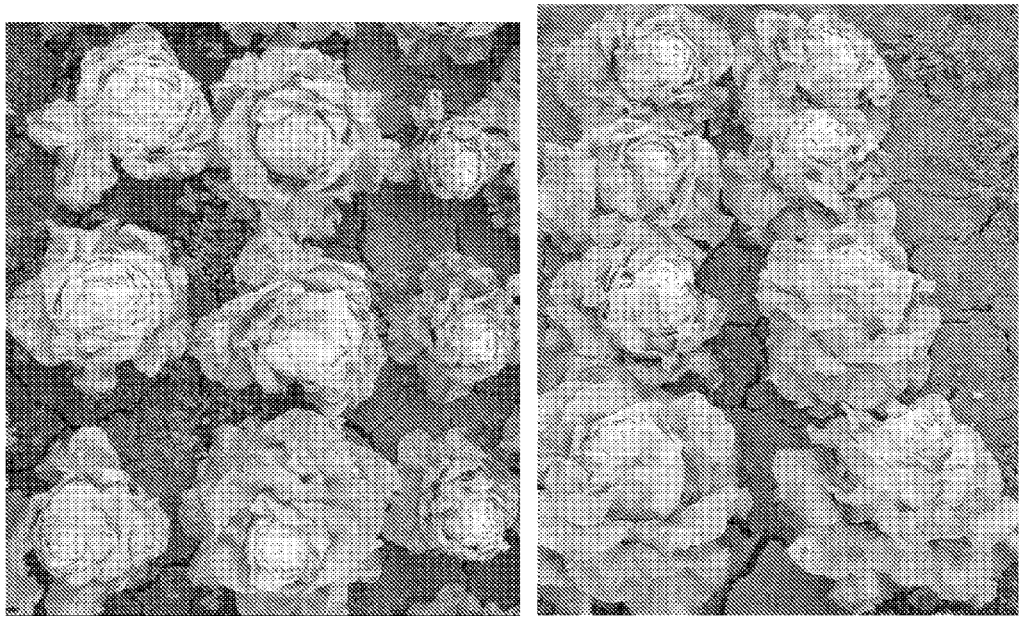
FIG. 11 compares quantitative variation in head size and the *B. lactucae* resistance response of four lettuce lines. From the left, the first two lines are cv. Sylvesta and cv. Olof, which represent agronomically elite germplasm, but are susceptible to *Bremia*. Olof is the line used to make the original interspecific cross a and the BILs. Sylvesta is the line used to develop recombined introgressions. The next line to the right is BIL6.3 that displays for *B. lactucae* resistance and a smaller diameter head. The final two rows on the right are line Q6-712 (see table 6). This line is a recombinant in the BIL6.3 region that retains the *B. lactucae* resistance trait, but eliminates the small diameter head and the bubbles trait. This line is characterized by markers LE3118 and LE9214.

The high resolution mapping results allowed for molecular identification of progeny plants that have recombined between the QTL for *Bremia* resistance and the QTL for horticultural traits on LG 6. These molecularly identified recombinants have phenotypic characteristics that concur with the molecular data. Examples of desirable recombinant lines that have the *L. saligna* marker alleles in the RBQ6 region and *L. sativa* marker alleles in the plant diameter and leaf bubbles QTL region are shown in Table 6. These lines have the higher disease resistance from *L. saligna*, and they have high plant diameter and low leaf bubble scores derived from *L. sativa*. FIG. 11 pictorially demonstrates using recombinant line Q6-712 as an example (see table 6), that a *Bremia* resistant line containing the RBQ6 resistant QTL is uncoupled from the deleterious trait of small head diameter.

deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 5,349,124
U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
An et al., *Plant Physiol.*, 88:547, 1988.
Beharav et al., *Genet Resource Crop Evol.* 53:467-474, 2006.
Bird et al., *Biotech. Gen. Engin. Rev.*, 9:207, 1991.
Bonnier et al., *Phytopathol.* 84:462-468, 1994
Bonnier et al., *Euphytica* 61: 203-211, 1992.
Broothaerts et al., *Nature* 433:629-633, 2005.
Bustos et al., *Plant Cell*, 1:839, 1989.
Callis et al., *Plant Physiol.*, 88:965, 1988.

TABLE 6

Characterization of recombinant lines that have retained the higher *Bremia* resistance from *L. saligna*, but have eliminated the defects in small plant diameter and leaf bubbling.

| | Phenotypes | | | Genotypes[1] | | | | | | |
|---|---|---|---|---|---|---|---|---|---|---|
| | Plant | | | | | | | | | |
| Line[2] | diameter[3] | Leaf bubbles[4] | Resistance[5] | LE3118 | LK1413 | LE0017 | LE9214 | LE0420 | LE0428 | LE1211 |
| Olof | 38.60 (2.32) | 3 | 5 | C | C | C | C | C | C | C |
| Sylvesta | 34.80 (2.90) | 1 | 9 | C | C | C | C | C | C | C |
| BIL6.3 | 29.40 (0.84) | 5 | 1 | D | D | D | D | D | D | D |
| Q6-10A6 | 33.55 (1.81) | 3.82 (0.40) | 3.00 (0.00) | D | D | D | D | C | C | C |
| Q6-10E2 | 33.92 (2.50) | 2.68 (0.67) | 3.66 (0.64) | D | D | D | D | C | C | C |
| Q6-4D2 | 32.42 (1.68) | 1.50 (0.52) | 3.34 (0.58) | D | D | D | D | C | C | C |
| Q6-4J2 | 33.33 (2.41) | 2.40 (0.51) | 2.86 (0.80) | D | D | D | D | C | C | C |
| Q6-5G1 | 34.31 (2.59) | 2.46 (0.66) | 5.16 (0.28) | D | D | D | D | C | C | C |
| Q6-7I2 | 37.64 (2.38) | 2.27 (0.90) | 2.28 (0.50) | D | D | D | D | C | C | C |
| Q6-9J5 | 35.73 (2.84) | 3.07 (0.70) | 4.46 (0.59) | D | D | D | D | C | C | C |

[1]Genotypes are scored with a 'D', indicating the presence of the donor (*L. saligna*) allele, or with a 'C', indicating the presence of the cultivated lettuce (*L. sativa*) allele. These genotypes are provided for 7 loci (LE3118, LK1413, LE0017, LE9214, LE0420, LE0428 and LE1211), that are contiguous on lettuce linkage group 6 (see FIGS. 2, 8 and 9). Protocols for molecular marker assays are found in example 1.
[2]Olof and Sylvesta are cultivated *L. sativa* lines that are susceptible to *Bremia*, but do not display the undesirable small plant diameter or leaf bubbling trait. BIL6.3. contains the *Bremia* resistance QTL RBQ6 as described by Jeuken et al. 2008. Lines Q6-10A6, Q6-10E2, Q6-4D2, Q6-4J2, Q6-5G1, Q6-7I2 and Q6-9J5 are recombinant lines derived from an original BIL6.3 x Sylvesta cross. These lines retain the RBQ6 *Bremia* resistance QTL, but do not suffer from the small plant diameter or increased leaf bubbling horticultural defects.
[3]Plant diameter was measured in cm as described in example 2. Data are means with standard deviations.
[4]Degree of leaf bubbles was measured in the as described in example 2. Field screening for *Bremia* relied on natural disease pressure, and plants were scored using a 1 to 9 scale (example 2). The recombinant lines are scored relative to the parental scores, and the means are reported with the standard deviations displayed parenthetically.
[5]*Bremia* resistance was measured in the summer as described in example 2. Plants were scored using a 1(resistant) to 9 (susceptible) scale. Means and standard deviations are reported, with the standard deviations displayed in parentheses.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are Choi et al., *Plant Cell Rep.*, 13: 344-348, 1994.
Chupeau et al., *Bio/Tech.*, 7:503-508, 1989.
Dekeyser et al., *Plant Cell*, 2:591, 1990.
Elliott et al., *Plant Cell Rep.*, 18:707-714, 2004.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Grube et al., *Euphytica* 142:205-215, 2005.
Gustafsson, *Euphytica*, 40: 227-232, 1989.
Jansen, *Genetics* 135:205-211, 1993.
Jansen, *Genetics* 138:871-881, 1994.

Jeuken et al., *Theor Appl Genet.* 103:638-647, 2001.
Jeuken et al., *Theor Appl Genet.* 105:384-391, 2002a.
Jeuken, M. "The Genetics of non-host resistance to the lettuce pathogen *Bremia* lactucae in *Lactuca saligna*". Ph.D. Thesis, Wageningen Univ. Dissertation #3203, ISBN 90-5808-619-4, 2002b.
Jeuken et al., *Theor Appl Genet.* 109:394-401, 2004.
Jeuken et al., *Theor Appl Genet.* 116:845-857, 2008.
Konieczny and Ausubel, *Plant J.* 4:403-410, 1993.
Klee et al., *Bio-Technology*, 3(7):637-642, 1985.
Kuhlemeier et al., *Plant Cell*, 1:471, 1989.
Lebeda et al., *Molecular Plant Pathology*, 44:125-139, 1995.
Lebeda et al., "Aspects of the Interactions Between Wild Lettuce Spp. and Related
Genera and Lettuce Down Mildew (*Bremia lactucae*)", pp. 85-117 in Advances in Downy Mildew Research, M. J. Jeger et al., eds. Kluwer Academic Publishers, Dordrecht, 2002.
Marcotte et al., *Nature*, 335:454, 1988.
Marcotte et al., *Plant Cell*, 1:969, 1989.
Molinier et al., *Plant Cell Rep.*, 21:251-256, 2002.
Netzer, *Hort. Sci.*, 11:612-613, 1976.
Norwood et al., *Euphytica* 32:161-170, 1983.
Odel et al., *Nature*, 313:810, 1985.
Omirulleh et al., *Plant Mol. Biol.*, 21(3):415-428, 1993.
Pang et al., *The Plant J.*, 9, 899-909, 1996.
Potrykus et al., *Mol. Gen. Genet.*, 199:183-188, 1985.
Reinink, "Lettuce Breeding," pp. 139-147 in Proc. EUCARPIA Meeting on Leafy Vegetables, Olomouc, Czech Republic, 1999.
Roshal et al., *EMBO J.*, 6:1155, 1987.
Ryder, In: *Breeding Vegetable Crops*, AVI Pub., Westport, Conn., 433-474, 1986.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Syed et al., *Theor Appl Genet.*, 112:517-27, 2006.
Terada and Shimamoto, *Mol. Gen. Genet.*, 220:389, 1990.
Uchimiya et al., *Mol. Gen. Genet.*, 204:204, 1986.
Van Ooijen & Voorrips, JoinMap® 3.0: Software for the calculation of genetic linkage maps. Plant Research International, Wageningen, the Netherlands, 2001.
Van Ooijen et al., MapQTL® 4.0, Software for the calculation of QTL positions on genetic maps. Plant Research International, Wageningen, the Netherlands, 2002.
Wang et al., *Science*, 280:1077-1082, 1998.
Williams et al., *Nucleic Acids Res.*, 1 8:6531-6535, 1990.
WO 99/31248

What is claimed is:

1. A lettuce seed comprising an allele conferring resistance to *Bremia lactucae*, wherein the seed lacks a second allele genetically linked to the allele conferring resistance in *Lactuca saligna*, wherein the second allele confers a trait selected from the group consisting of adventitious shoots, reduced plant diameter and bubbled leaves, wherein the allele conferring resistance to *Bremia lactucae* is selected from the group consisting of (a) a RBQ5 allele of *Lactuca saligna* conferring quantitative resistance to *Bremia lactucae*, wherein the seed lacks an allele genetically linked to the RBQ5 allele in *Lactuca saligna* conferring adventitious shoots, and (b) a RBQ6 allele of *Lactuca saligna* conferring quantitative resistance to *Bremia lactucae*, wherein the seed lacks an allele genetically linked to the RBQ6 allele in *Lactuca saligna* conferring reduced plant diameter or bubbled leaves.

2. The lettuce seed of claim 1, comprising the RBQ5 allele and the RBQ6 allele.

3. The lettuce seed of claim 1, further defined as comprising at least one additional gene that confers resistance to *Bremia lactucae*, wherein the gene is selected from the group consisting of DM1 to DM16 and R17 to R40.

4. The lettuce seed of claim 1, comprising the RBQ5 allele.

5. The lettuce seed of claim 1, comprising the RBQ6 allele.

6. A lettuce seed comprising a chromosomal segment that comprises a RBQ6 allele of *Lactuca saligna* conferring quantitative resistance to *Bremia lactucae* and lacking a *Lactuca saligna* allele genetically linked thereto that confers reduced plant diameter or bubbled leaves, wherein a representative sample of seed comprising the chromosomal segment was deposited under ATCC Accession Number PTA-9045.

7. A lettuce seed comprising a chromosomal segment that comprises a RBQ5 allele of *Lactuca saligna* conferring quantitative resistance to *Bremia lactucae* and lacking a *Lactuca saligna* allele genetically linked thereto that confers adventitious shoots, wherein a representative sample of seed comprising the chromosomal segment was deposited under ATCC Accession Number PTA-9046.

8. A lettuce seed comprising an introgressed *L. saligna* region comprising an LE1244 allele and wherein the plant lacks an *L. saligna* LE1219 and/or LE0115 allele.

9. A lettuce seed comprising an introgressed *L. saligna* region comprising an LE9214 and/or LE0017 allele, and wherein the plant lacks an *L. saligna* LE0420 allele.

10. A lettuce plant comprising an introgressed *L. saligna* region comprising an LE0142 allele, and wherein the plant lacks an *L. saligna* LE1219 and/or LE0115 allele.

11. A lettuce plant comprising an introgressed *L. saligna* region comprising an LK1413 and/or LE3118 allele, and wherein the plant lacks an *L. saligna* LE0420 allele.

12. A lettuce seed comprising an introgressed *L. saligna* region comprising an LE0142 allele, and wherein the plant lacks an *L. saligna* LE1219 and/or LE0115 allele.

13. A lettuce seed comprising an introgressed *L. saligna* region comprising an LK1413 and/or LE3118 allele, and wherein the plant lacks an *L. saligna* LE0420 allele.

* * * * *

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
ggagttcagg gcctctgtc                                                   19

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ccgattctgc ggttatcttc                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
tttgggttcc ttcagtttgc                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
```
cacagtttgg gatgaacacg                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
cggttgctca agacctctca                                              20

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
agcgaacgac cctctaacg                                               19

<210> SEQ ID NO 7
<211> LENGTH: 22
<212> TYPE: DNA
<213> ORGANISM: Artificial Sequence
<220> FEATURE:
<223> OTHER INFORMATION: Synthetic primer

<400> SEQUENCE: 7
ggaggttcat ggcctacttt ac                                           22

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
ggctcaatga ctgacacttg c                                            21

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
cgttgacaac cactcaccac                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
actgaagttt ttggcgaagc                                              20

<210> SEQ ID NO 11
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 11
gaaaccagag gaggcagttg                                               20

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
gtgctgcttc ttacaaccaa ac                                            22
```